US006316631B1

(12) United States Patent
Chen et al.

(10) Patent No.: US 6,316,631 B1
(45) Date of Patent: *Nov. 13, 2001

(54) PROCESS FOR CONVERTING 2,4-DICHLOROPYRIDINES INTO 2-ARYLOXY-4-CHLOROPYRIDINES

(75) Inventors: Yuhpyng L. Chen; Sally Gut Ruggeri, both of Waterford, CT (US)

(73) Assignee: Pfizer Inc., New York, NY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/254,387
(22) PCT Filed: Jun. 6, 1995
(86) PCT No.: PCT/IB95/00437
  § 371 Date: Mar. 4, 1999
  § 102(e) Date: Mar. 4, 1999
(87) PCT Pub. No.: WO96/39388
  PCT Pub. Date: Dec. 12, 1996
(51) Int. Cl.[7] ............... C07D 213/64; C07D 213/643
(52) U.S. Cl. ........................... 546/302; 546/303
(58) Field of Search ................... 546/302, 303

(56) References Cited

U.S. PATENT DOCUMENTS

| 3,637,720 | 1/1972 | Nishiyama | 546/300 |
|---|---|---|---|
| 4,655,824 | * 4/1987 | Mengel et al. | 71/94 |
| 4,786,317 | * 11/1988 | Mengel et al. | 71/94 |
| 4,925,947 | * 5/1990 | Cartwright | 546/302 |
| 5,032,168 | * 7/1991 | Turner | 71/92 |

FOREIGN PATENT DOCUMENTS

| 0154538 | 3/1982 | (DD) . |
|---|---|---|
| 0315916 | 5/1989 | (EP) . |
| 0385720 | 9/1990 | (EP) . |
| 7900094 | 3/1979 | (WO) . |

OTHER PUBLICATIONS

Evans, et al., J. Am. Chem. Soc. 1989, III, pp. 1063–1072 – The Total Synthesis of the Isodityrosine–Derived Cyclic Tripeptides of 4949–III and K–13. Determination of the Absolute Configuration of K–13.

Williams, et al. Solvent–assisted Ullmann Ether Synthesis, Reactions of Dihydricphenols, J. Org. Chem. 32, pp. 2501–2505 (1967).

Schmidt, et al., Total Synthesis of 4924–III, a natural inhibitor of amino–peptidase B from Ehrlich Asates Carcinoma Cells, Tetra. Ltrs, 29(26) pp. 3227–3230(1988).

Reagents for Organic Synthesis, vol. I, Fieser, et al., 1972, p. 68.

Reagents for Organic Synthesis, vol. 9, Fieser, et al., 1981, pp.125.

* cited by examiner

Primary Examiner—Alan L. Rotman
(74) Attorney, Agent, or Firm—Peter C. Richardson; Paul H. Ginsburg; Grover F. Fuller Jr.

(57) ABSTRACT

This invention relates to a process for converting 2,4-dichloropyridines into 2-aryloxy-4-chloropyridines, comprising reacting a compound of formula (I), wherein $R^1$ is $(C_1-C_4)$alkyl; $R^2$ is methyl or ethyl; and $R^3$, $R^4$ and $R^5$ are selected, independently, from $(C_1-C_4)$alkyl and $(C_1-C_4)$alkoxy; or a pharmaceutically acceptable salt thereof; comprising reacting a compound of formula (II), wherein $R^1$ and $R^2$ are defined as above, with a compound of formula (III), wherein $R^3$, $R^4$ and $R^5$ are defined as above, in the presence of a base that is capable of deprotonating the compound of formula (III), optionally in the presence of an organometallic halide or oxide and a suitable solvent, and then optionally converting the resulting compound of formula (I) into a pharmaceutically acceptable salt of such compound.

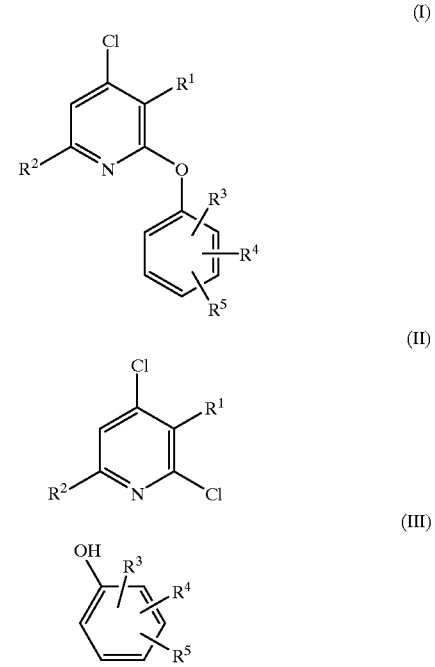

6 Claims, No Drawings

US 6,316,631 B1

PROCESS FOR CONVERTING 2,4-DICHLOROPYRIDINES INTO 2-ARYLOXY-4-CHLOROPYRIDINES

BACKGROUND OF THE INVENTION

This invention relates to a process for converting 2,4-dichloropyridines into 2-aryloxy-4-chloropyridines. This process can be used to prepare 3,6-di-$(C_1-C_4)$alkyl-4-chloro-2-(2,4,6-trisubstitutedphenoxy)pyridines, which are intermediates in the synthesis of pharmaceutically active 2-phenoxy-pyridine derivatives that exhibit activity as corticotropin releasing factor (CRF) antagonists and are useful in the treatment of several neurological disorders. Such pharmaceutically active compounds, methods of preparing them and the neurological disorders that they are useful in treating are described in copending U.S. patent application No. 08/255,514, which was filed on Jun. 8, 1994, (now abandoned), which is a 371 of PCT/IB95/00439 filed Jun. 6, 1995, which issued as WO 953370 Dec. 14, 1995. This PCT International Application is incorporated herein by reference in its entirety.

SUMMARY OF THE INVENTION

This invention relates to a process for preparing a compound of the formula

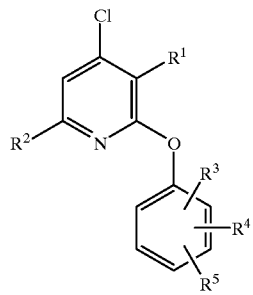

I wherein $R^1$ is $(C_1-C_4)$alkyl;
$R^2$ is methyl or ethyl; and $R^3$, $R^4$ and $R^5$ are selected, independently, from $(C_1-C_4)$alkyl and $(C_1-C_4)$alkoxy; or a pharmaceutically acceptable salt thereof; comprising reacting a compound of the formula

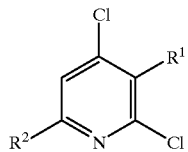

II wherein $R^1$ and $R^2$ are defined as above, with a compound of the formula

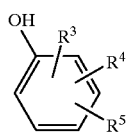

III wherein $R^3$, $R^4$ and $R^5$ are defined as above, in the presence of a base that is capable of deprotonating the compound of formula III, optionally in the presence of an organometallic halide or oxide and a suitable solvent, and then optionally converting the resulting compound of formula I into a pharmaceutically acceptable salt of such compound.

Suitable bases for this reaction include sodium hydride, potassium hydride, potassium carbonate, cesium carbonate, ammonium hydroxide, n-butyllithium and lithium, sodium or potassium $(C_1-C_4)$ alkoxide. Examples of suitable solvents are tetrahydrofuran (THF), dimethylsulfoxide (DMSO), acetonitrile, methylene chloride ($CH_2Cl_2$), 1-methyl-2-pyrrolidinone, pyridine, quinoline, N,N-dialkylformamide (e.g. N,N-dimethylformamide), hexamethyl phosphormamide and toluene. The reaction temperature may range from about 0° to about 180° C. and is preferably between about room temperature and about 150° C.

A preferred embodiment of this invention relates to the above process wherein the compound of formula I that is formed is a compound wherein all of $R^1$, $R^2$, $R^3$ and $R^4$ and $R^5$ are methyl, the solvent is pyridine, the organometallic halide or oxide is copper (I) iodide and the base is potassium t-butoxide.

Another embodiment of this invention relates to the above depicted reaction of a compound of the formula II with a compound of the formula III, wherein the solvent is selected from dimethylsulfoxide (DMSO), pyridine, 2,4,6-trimethylpyridine, quinoline, and mixtures of the foregoing solvents, the base is selected from potassium hydride, sodium hydride, sodium methoxide, potassium t-butoxide, and sodium t-butoxide, and the organometallic halide or oxide is selected from cuprous bromide, cuprous chloride and cuprous iodide.

Other embodiments of this invention relates to the above depicted reaction of the compound of formula II with a compound of the formula III, wherein:

(a) the solvent is pyridine, DMSO or a mixture of pyridine and DMSO; or (b) the base is sodium hydride or potassium t-butoxide; or (c) the organometallic halide or oxide is cuprous iodide, cuprous bromide or cuprous chloride;

(d) the solvent is pyridine, $R^1$ and $R^2$ in the compound of formula II are both methyl and $R^3$, $R^4$ and $R^5$ in the compound of formula II are both methyl and $R^3$, $R^4$ and $R^5$ in the compound of formula III are all methyl;

(e) the solvent is pyridine, $R^1$ through $R^5$ in formulae II and III are all methyl and the base is potassium t-butoxide; or (f) the solvent is pyridine, $R^1$ through $R^5$ in formulae II and III are all methyl, and the organometallic halide or oxide is cuprous iodide, cuprous bromide or cuprous chloride.

DETAILED DESCRIPTION OF THIS INVENTION

Compound of the formula I are useful as intermediates in the synthesis of 2-phenoxy-pyridine derivatives that are cotricotropin releasing factor (CRF) antagonists and are useful in the treatment of disorders for which treatment can be effected or facilitated by antagonizing CRF. Examples of such disorders are those selected from inflammatory disorders such as rheumatoid arthritis and osteoarthritis, pain, asthma, psoriasis and allergies; generalized anxiety disorder; panic; phobias; obsessive-compulsive disorder; post-traumatic stress disorder; sleep disorders induced by stress; pain perception such as fibromyalgia; mood disorders such as depression, including major depression, single episode depression, recurrent depression, child abuse induced depression, and postpartum depression; dysthemia; bipolar disorders; cyclothymia; fatigue syndrome; stress-induced headache; cancer; irritable bowel syndrome, Crohn's disease; spastic colon; human immunodeficiency virus (HIV) infections; neurodegenerative diseases such as Alzheimer's disease, Parkinson's disease and Huntington's disease; gastrointestinal diseases; eating disorders such as anorexia and bulimia nervosa; hemorrhagic stress; chemical dependencies and addictions (e.g., dependencies on alcohol, cocaine, heroin, benzodiazepines, or other drugs); drug and alcohol withdrawal symptoms; stress-induced psychotic episodes; euthyroid sick syndrome; syndrome of unappropriate antidiarrhetic hormone (ADH); obesity; infertility; head traumas; spinal and cord trauma; ischemic neuronal damage (e.g., cerebral ischemia such as cerebral hippocampal ischemia); excitotoxic neuronal damage (e.g., cerebral ischemia such as cerebral hippocampal ischemia); excitotoxic neuronal damage; epilepsy; stroke; immune disfunctions including stress induced immune dysfunctions (e.g., porcine stress syndrome, bovine shipping fever, equine paroxysmal fibrilation, and dysfunctions induced by confinement in chickens, sheering stress in sheep or human-animal interaction related stress in dogs); muscular spasms; urinary incontinence; senile dementia of the Alzheimer's type; multiinfarct dementia; amyotrophic lateral sclerosis; and hypoglycemia in mammals, including humans.

The pharmaceutically active CRF antagonists that can be prepared using the intermediates of formula I that are produced by the processes of this invention are depicted below.

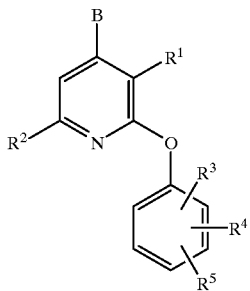

In these compounds, B is —NR$^6$R$^7$, —NHCHR$^6$R$^7$, —OCHR$^6$R$^7$ or —SCHR$^6$R$^7$;

R$^1$ through R$^5$ are defined as above;

R$^6$ is C$_1$–C$_6$ alkyl which may optionally be substituted with one or two substituents R$^8$ independently selected from the group consisting of hydroxy, fluoro, chloro, bromo, iodo, CF$_3$ and C$_1$–C$_4$ alkoxy, and wherein said C$_1$–C$_6$ alkyl and the (C$_1$–C$_4$)alkyl moiety of said C$_1$–C$_4$ alkoxy may optionally contain one carbon-carbon double or triple bond; and R$^7$ is C$_1$–C$_{12}$ alkyl, aryl or —(C$_1$–C$_4$ alkylene)aryl wherein said aryl is phenyl, napthyl, thienyl, benzothienyl, pyridyl, quinolyl, pyrazinyl, pyrimidyl, imidazolyl, furanyl, benzofuranyl, benzothiazolyl, isothiazolyl, benzisothiazolyl, benzisoxazolyl, benzimidazolyl, indolyl, or benzooxazolyl; 3- to 8-membered cycloalkyl or —(C$_1$–C$_6$ alkylene)cycloalkyl, wherein one or two of the ring carbons of said cycloalkyl having at least 4 ring members and the cycloalkyl moiety of said —(C$_1$–C$_6$ alkylene)cycloalkyl having at least 4 ring members may optionally be replaced by an oxygen or sulfur atom or by N—R$^9$ wherein R$^9$ is hydrogen or C$_1$–C$_4$ alkyl; and wherein each of the foregoing R$^7$ groups may optionally be substituted with from one to three substituents independently selected from chloro, fluoro and C$_1$–C$_4$ alkyl, or with one substituent selected from bromo, iodo, C$_1$–C$_6$ alkoxy, —O—CO—(C$_1$–C$_6$ alkyl), —O—CO—N(C$_1$–C$_4$ alkyl)(C$_1$–C$_2$ alkyl), —S(C$_1$–C$_6$ alkyl), CN NO$_2$, —SO(C$_1$–C$_4$ alkyl), and —SO$_2$(C$_1$–C$_4$ alkyl), and wherein said C$_1$–C$_{12}$ alkyl and the C$_1$–C$_4$ alkylene moiety of said —(C$_1$–C$_4$ alkylene)aryl may optionally contain one carbon-carbon double or triple bond;

or —NR$^7$R$^7$ may form a saturated 5- to 8-membered carbocyclic ring which may optionally contain one or two carbon-carbon double bonds and in which one or two of the ring carbons may optionally be replaced by an oxygen or sulfur atom.

The pharmaceutically active compounds depicted above are described in copending U.S. patent application No. 08/255.514, which was filed on Jun. 8, 1994 and which is incorporated herein by reference in its entirety. Methods of preparing such compounds and their pharmaceutically acceptable salts (hereinafter collectively referred to as "the active agents") are also set forth in that application.

The active agents can be administered alone or in combination with pharmaceutically acceptable carriers, in either single or multiple doses. Suitable pharmaceutical carriers include inert solid diluents or fillers, sterile aqueous solutions and various organic solvents. The pharmaceutical compositions formed by combining compounds of the formula I and pharmaceutically acceptable carriers can be readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, methylcellulose, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tableting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions containing an active agent in sesame or peanut oil, aqueous propylene glycol or a sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art.

The effective dosages for the active agents will depend on the intended route of administration and factors such as the age, weight and condition of the patient, as generally known to a physician. The dosage will also depend on the particular illness to be treated. The daily dosage for stress-induced illnesses, inflammatory disorders, Alzheimer's disease, gastrointestinal diseases, anorexia nervosa, hemorrhagic stress and drug and alcohol withdrawal symptoms will generally range from about 0.1 to about 50 mg/kg body weight of the patient to be treated.

The following experimental example illustrates the novel process of this invention but does not limit its scope.

EXAMPLE 1

4-Chloro-3,6-dimethyl-2-(2,4,6-trimethylphenoxy)-pyridine

To a 2 liter flask equipped with a mechanical stirrer, a reflux condenser and a nitrogen inlet was charged 250 ml of pyridine. The flask was cooled in an ice bath and charged with 42.5 g (0.312 mmol) of 2,4,6-trimethylphenol and 35.1 g (0.313 mol) of potassium t-butoxide. The flask was warmed to room temperature and charged with 50.0 g (0.284 mol) of 2,4-dichloro-3,6-dimethylpyridine and 13.5 g (0.071 mol) of copper (I) iodide. The reaction mixture was heated to reflux for two hours and then cooled to 0° C. The reaction was diluted with 500 ml of hexanes, then mixed with 1000 ml of saturated ammonium chloride ($NH_4Cl$). After warming to room temperature, the mixture was stirred overnight. The layers were separated and the organic layer was washed with 3×125 ml of 1M ammonium hydroxide ($NH_4OH$), 2×250 ml of 3N sodium hydroxide (NaOH), 1×250 ml of 1N hydrochloric acid (HCl) and 1×250 ml of water. After drying over sodium sulfate ($Na_2SO_4$), the solids were removed by filtration and washed with hexane. The filtrate was concentrated under vacuum to a brown oil. The residue was mixed with 250 ml methanol and stirred overnight. The resulting slurry was filtered under vacuum. The off-white solids were washed with methanol then dried to obtain 31.6 g (40.4%) of the title compound.

$^1$H NMR ($CDCl_3$): 6.88 (s, 2H), 6.78 (s, 1H), 2.40 (s, 3H). 2.20 (s, 3H), 2.04 (s, 6H) ppm.

The filtrate was concentrated under vacuum to an oil and the residue was mixed with 50 ml of methanol. After stirring overnight, the resulting slurry was cooled to 0° C. and filtered under vacuum. The solids were washed with minimal methanol and dried to give an additional 16.1 g (20.5%) of material.

What is claimed is:

1. A process for preparing a compound of the formula

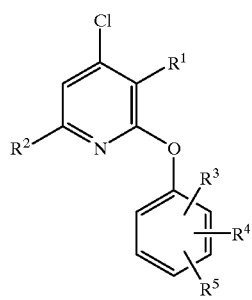

I wherein $R^1$ is ($C_1$–$C_4$)alkyl; $R^2$ is methyl or ethyl; and $R^3$, $R^4$ and $R^5$ are selected, independently, from ($C_1$–$C_4$)alkyl and ($C_1$–$C_4$)alkoxy; or a pharmaceutically acceptable salt thereof; comprising reacting a compound of the formula

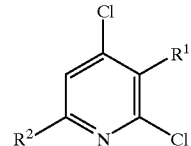

II wherein $R^1$ and $R^2$ are defined as above, with a compound of the formula

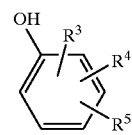

III wherein $R^3$, $R^4$ and $R^5$ are defined as above, in the presence of a base that is capable of deprotonating the compound of formula III, in the presence of copper (I) bromide, copper (I) chloride, or copper (I) iodide and pyridine, and then optionally converting the resulting compound of formula I into a pharmaceutically acceptable salt of such compound.

2. A process according to claim 1, wherein the base is selected from sodium hydride, potassium hydride, potassium carbonate, cesium carbonate, ammonium hydroxide, lithium ($C_1$–$C_4$)alkoxide, sodium or potassium ($C_1$–$C_4$) alkoxide and n-butyllithium.

3. A process according to claim 1 which produces a compound of the formula I wherein all of $R^1$, $R^2$, $R^3$, $R^4$ and $R^5$ are methyl.

4. A process according to claim 1 wherein the base is potassium t-butoxide.

5. A process according to claim 3, wherein the base is potassium t-butoxide.

6. A process according to claim 1 wherein the base is sodium hydride or potassium t-butoxide.

* * * * *